US009006678B2

(12) United States Patent
Ivashin et al.

(10) Patent No.: US 9,006,678 B2
(45) Date of Patent: Apr. 14, 2015

(54) NON-RADIOACTIVE ION SOURCE USING HIGH ENERGY ELECTRONS

(71) Applicant: Implant Sciences Corporation, Wilmington, MA (US)

(72) Inventors: Dmitriy V. Ivashin, Peabody, MA (US); Säid Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 0 days.

(21) Appl. No.: 13/960,006

(22) Filed: Aug. 6, 2013

(65) Prior Publication Data
US 2014/0034844 A1   Feb. 6, 2014

Related U.S. Application Data

(60) Provisional application No. 61/679,976, filed on Aug. 6, 2012.

(51) Int. Cl.
*H01J 27/00*    (2006.01)
*H01J 31/04*    (2006.01)
(Continued)

(52) U.S. Cl.
CPC ............. *H01J 31/04* (2013.01); *H01J 29/04* (2013.01); *H01J 27/205* (2013.01); *H01J 3/021* (2013.01); *H01J 33/02* (2013.01); *G01N 27/624* (2013.01)

(58) Field of Classification Search
USPC ............ 250/423 R, 424, 427, 423 P, 281, 288
See application file for complete search history.

(56) References Cited

U.S. PATENT DOCUMENTS 3,809,889 A * 5/1974 McBroom ............... 250/214 VT
4,146,787 A    3/1979 Fite
(Continued)

FOREIGN PATENT DOCUMENTS

DE    102 48 055 A1    4/2004
JP    H0325846         2/1991

OTHER PUBLICATIONS

A.D. Appelhans and D.A. Dahl, "SIMION ion optics simulation at atmospheric pressure," *Int. J. Mass. Spectrom*, 244 (2005), pp. 1-14.
(Continued)

*Primary Examiner* — Michael Logie
*Assistant Examiner* — Jason McCormack
(74) *Attorney, Agent, or Firm* — Muirhead and Saturnelli, LLC

(57) ABSTRACT

A system and method for producing a continuous or pulsed source of high energy electrons at or near atmospheric pressure is disclosed. High energy electrons are used to ionize analyte molecules in ambient air through collisions with reactant ions. The device includes an electron emitter, electron optics, and a thin membrane in an evacuated tube. The electron emitter may include a photocathode surface mounted on an optically transparent window and an external source of UV photons. The transparent window may include a UV transparent window mounted on an evacuated tube and/or the evacuated tube may be a transparent tube on which a photocathode surface film is deposited. The electron optics may include successive electrodes biased at increasing voltages. The membrane may include a material transparent or semi-transparent to energetic electrons. Upon impacting the membrane, continuous or pulsed electron packets are partially transmitted through to a high pressure ionization region.

24 Claims, 4 Drawing Sheets

(51) Int. Cl.
    *H01J 29/04*    (2006.01)
    *H01J 27/20*    (2006.01)
    *H01J 3/02*     (2006.01)
    *H01J 33/02*    (2006.01)
    *G01N 27/62*    (2006.01)

(56) References Cited

U.S. PATENT DOCUMENTS

| | | | |
|---|---|---|---|
| 4,476,392 A | * | 10/1984 | Young .................. 250/423 R |
| 4,733,086 A | * | 3/1988 | Simmonds ............. 250/423 P |
| 5,338,931 A | | 8/1994 | Spangler et al. |
| 5,561,697 A | | 10/1996 | Takafuji et al. |
| 5,969,349 A | * | 10/1999 | Budovich et al. ............ 250/286 |
| 6,329,769 B1 | | 12/2001 | Naito |
| 6,429,426 B1 | | 8/2002 | Döring |
| 6,677,581 B1 | | 1/2004 | Koinuma et al. |
| 7,105,808 B2 | | 9/2006 | Bromberg et al. |
| 7,510,666 B2 | | 3/2009 | Walton et al. |
| 7,576,320 B2 | | 8/2009 | Bunker et al. |
| 7,898,160 B2 | | 3/2011 | Aizawa et al. |
| 8,173,959 B1 | | 5/2012 | Boumsellek et al. |
| 8,440,981 B2 | | 5/2013 | Bromberg et al. |
| 2005/0173629 A1 | | 8/2005 | Miller et al. |
| 2007/0181818 A1 | * | 8/2007 | Austin .................... 250/373 |
| 2007/0272852 A1 | | 11/2007 | Miller et al. |
| 2009/0095917 A1 | | 4/2009 | Doring et al. |
| 2009/0261263 A1 | * | 10/2009 | Menge et al. ............ 250/370.11 |
| 2012/0160997 A1 | | 6/2012 | Fink et al. |
| 2012/0273669 A1 | | 11/2012 | Ivashin et al. |
| 2012/0326020 A1 | | 12/2012 | Ivashin et al. |

OTHER PUBLICATIONS

I. A. Buryakov et al., "A new method of separation of multi-atomic ions by mobility at atmospheric pressure using a high-frequency amplitude-asymmetric strong electric field," International Journal of Mass Spectrometry and Ion Processes, vol. 128, Issue 3, Oct. 9, 1993, pp. 143-148.

E. V. Krylov, et al., "Selection and generation of waveforms for differential mobility spectrometry," Review of Scientific Instruments, 81, 024101 (2010), 11 pp.

U.S. Appl. No. 13/858,417, filed Apr. 8, 2013, Ivashin et al.

* cited by examiner

NON-RADIOACTIVE ION SOURCE USING HIGH ENERGY ELECTRONS

RELATED APPLICATIONS

This application claims priority to U.S. Provisional App. No. 61/679,976, filed Aug. 6, 2012, entitled "High Energy Electron Source," which is incorporated herein by reference.

TECHNICAL FIELD

This application is related to the field of chemical analysis and, in particular, ion mobility spectrometry.

BACKGROUND OF THE INVENTION

In field applications, chemical analysis instruments may be confronted with various complex mixtures regardless of indoor or outdoor environments. Such mixtures may cause instrument contamination and confusion due to the presence of molecular interferents producing signatures that are either identical to that of the chemical compounds of interest or unresolved by the analytical instrument due to its limited resolution. An interferent can also manifest its presence by affecting the limit of detection of the compound of interest. A multi-stage analysis approach may therefore be used to reduce the chemical noise and produce enough separation for deterministic detection and identification. The multi-stage analysis may include either a single separation technique such as mass spectrometry (MS) in MS$^n$ instruments or a combination of different separation techniques, such as mass spectrometry and ion mobility spectrometry. These are called orthogonal techniques since, even though they may operate in tandem, they measure different properties of the same molecule by producing multi-dimensional spectra hence increasing the probability of detection and accuracy of detection. For field instruments, such techniques may be physically and operationally integrated in order to produce complementary information hence improving overall selectivity without sacrificing speed and sensitivity.

Ion Mobility Spectrometers (IMS) using radioactive ionization have been the workhorse of trace explosives detection at passenger checkpoints in airports. The technique relies on the availability of sufficient explosives residue (particles and/or vapor) on the passenger skin, clothing, and personnel items to signal a threat. The assumption being that due to their high sticking coefficient it is difficult to avoid contamination by explosives particles during the process of handling a bomb. The same high sticking coefficient results in extremely low vapor pressures and hence makes their detection difficult. The acquisition of vapor and/or particle samples may be achieved by either swiping "suspect" surfaces of luggage or persons, or in the case of portals and/or by sending pulses of compressed air intended to liberate particles off the person's clothing, skin, shoes etc. . . . In both cases the sample is introduced into an IMS for analysis.

Ion mobility spectrometry utilizes relative low electric fields to propel ions through a drift gas chamber and separate these ions according to their drift velocity. In IMS, the ion drift velocity is proportional to the field strength and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum. Since different molecules may have similar drift times, IMS inherently has limited chemical specificity and therefore is vulnerable to interfering molecules.

Other mobility-based separation techniques include high-field asymmetric waveform ion mobility spectrometry (FAIMS) also known as Differential Mobility Spectrometry (DMS). FAIMS or DMS is a detection technology which can operate at atmospheric pressure to separate and detect ions, as first described in detail by I. A. Buryakov et al., International Journal of Mass Spectrometry and Ion Processes 1993, 128 (3), pp. 143-148, which is incorporated herein by reference. FAIMS separates ions by utilizing the mobility differences of ions at high and low fields. Compared to conventional ion mobility, FAIMS operates at much higher fields (~10,000 V/cm) where ion mobilities become dependent on the applied field and are better represented by $K_h$, a non-constant high-field mobility term. Variations in $K_h$ from the low-field K, and the compound-dependence of that variation aids FAIMS in its separation power. FAIMS utilizes a combination of alternating current (AC) and direct current (DC) voltages to transmit ions of interest and filter out other ions, thus improving specificity, and decreasing the chemical noise. FAIMS can reduce false positives, since two different compounds having the same low-field mobility can often be distinguished in a high-field environment.

Known atmospheric pressure ionization devices, such as the ones used in IMS and FAIMS (DMS) devices, may use a radioactive ionization source to generate the ions that are used in connection with the chemical analysis and detection processes. Still other known devices may use non-radioactive ionization techniques that include corona discharges and/or ultraviolet (UV) light and laser-induced ionization. Radioactive sources such as $^{63}N_i$ are continuous sources of beta particles or high energy electrons (tens of keV). It has further been recognized that electron beams generated using non-radioactive means may be used as non-radioactive ionization sources for atmospheric pressure chemical ionization devices. In connection with the above-noted techniques, reference is made, for example, to U.S. Pat. No. 8,440,981 to Bromberg et al., entitled "Compact Pyroelectric Sealed Electron Beam," U.S. Pat. No. 6,429,426 to Döring, entitled "Ionization Chamber with Electron Source," and U.S. Pat. No. 5,969,349 to Budovich et al., entitled "Ion Mobility Spectrometer," all of which are incorporated herein by reference. The use of non-radioactive ionization sources beneficially avoids certain health hazards as well as travel and legal restrictions on radioactive sources.

Accordingly, it would be desirable to provide a non-radioactive ion source for use in chemical analysis and detection devices that provides beneficial enhancements and efficiencies over known ionization devices.

SUMMARY OF THE INVENTION

According to the system described herein, a high energy electron source device for ionization includes an electron emitter disposed within an evacuated tube behind an optically transparent portion of the evacuated tube. The electron emitter includes a photocathode element that emits electrons when excited by photons received at the photocathode element through the optically transparent portion of the evacuated tube. Electron optics may accelerate and/or focus electrons to control the flow of electrons along the evacuated tube. A membrane is disposed at an end of the evacuated tube downstream from the flow of electrons caused by the electron optics, wherein the electrons arriving at the membrane from the electron optics pass through the membrane to yield high energy electrons. The electron optics may include a plurality of electrodes disposed along the evacuated tube, wherein the plurality of electrodes are based at increasing voltages to control a final electron energy of the electrons arriving at the membrane. The photocathode element may be a photocathode surface film deposited on the optically transparent portion of the evacuated tube and/or the photocathode element is at least one of: a solid, a mesh, a needle, or a wire made of electrically conducting material. The evacuated tube may be a transparent tube made of a UV transparent material and/or the evacuated tube is a non-transparent tube having a transparent window as the optically transparent portion. The membrane may be a non-metallic thin film.

According further to the system described herein, a method for producing high energy electrons for ionization includes exciting an electron emitter disposed within an evacuated tube behind an optically transparent portion of the evacuated tube. The electron emitter includes a photocathode element that emits electrons when excited by photons received at the photocathode element through the optically transparent portion of the evacuated tube. A flow of the electrons along the evacuated tube is controlled using electron optics. The electrons are passed through a membrane disposed at an end of the evacuated tube downstream from the flow of electrons caused by the electron optics, wherein the electrons that pass through the membrane are high energy electrons. The electron optics may include a plurality of electrodes disposed along the evacuated tube, wherein the plurality of electrodes are based at increasing voltages to control a final electron energy of the electrons arriving at the membrane. The photocathode element may be a photocathode surface film deposited on the optically transparent portion of the evacuated tube and/or the photocathode element is at least one of: a solid, a mesh, a needle, or a wire made of electrically conducting material. The evacuated tube may be a transparent tube made of a UV transparent material and/or the evacuated tube is a non-transparent tube having a transparent window as the optically transparent portion. The membrane may be a non-metallic thin film.

According further to the system described herein, an ion source device includes an electron emitter disposed within an evacuated tube behind an optically transparent portion of the evacuated tube. The electron emitter includes a photocathode element that emits electrons when excited by photons received at the photocathode element through the optically transparent portion of the evacuated tube. A flow of the electrons along the evacuated tube is controlled using electron optics. The electrons are passed through a membrane disposed at an end of the evacuated tube downstream from the flow of electrons caused by the electron optics, wherein the electrons that pass through the membrane are high energy electrons. An ionization zone is disposed downstream from the membrane and in which reactant ions are generated, the reactant ions being generated from analyte molecules using the high energy electrons. An ion selection component receives the reactant ions propelled from the ionization zone and delivers selected reactant ions to a sample zone, wherein the reactant ions from the ionization zone are selectively separated or filtered to generate the selected reactant ions, and wherein, in the sample zone, the selected reactant ions react with sample molecules of interest of a sample being analyzed in a charge transfer process. The electron optics may include a plurality of electrodes disposed along the evacuated tube, wherein the plurality of electrodes are based at increasing voltages to control a final electron energy of the electrons arriving at the membrane. The photocathode element may be a photocathode surface film deposited on the optically transparent portion of the evacuated tube and/or the photocathode element is at least one of: a solid, a mesh, a needle, or a wire made of electrically conducting material. The evacuated tube may be a transparent tube made of a UV transparent material and/or the evacuated tube is a non-transparent tube having a transparent window as the optically transparent portion. The membrane may be a non-metallic thin film.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

Figure 1:
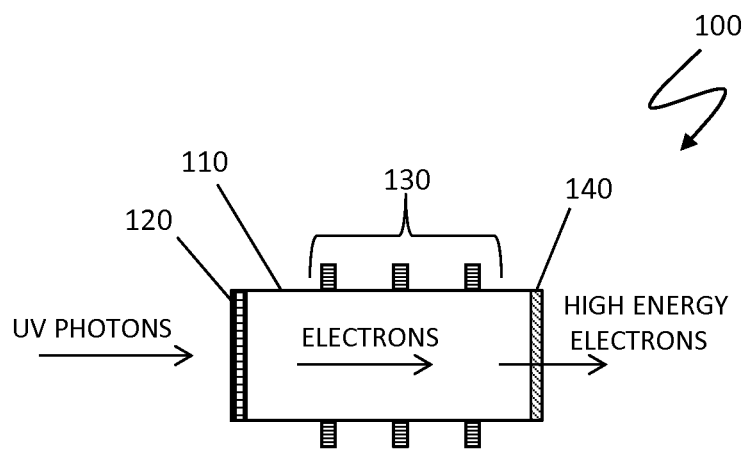
FIG. 1 is a schematic illustration showing a high energy electron source device for producing continuous or pulsed source of high energy electrons at atmospheric or near atmospheric pressure according to an embodiment of the system described herein.

FIG. 1 is a schematic illustration showing a high energy electron source device 100 for producing continuous or pulsed source of high energy electrons at atmospheric or near atmospheric pressure according to an embodiment of the system described herein. According to the system described herein, high energy electrons may be used to efficiently ionize analyte molecules in ambient air through collisions with reactant ions. Compared to conventional radioactive emitters such a non-radioactive high energy ion source eliminates the health hazards, travel and legal restrictions as well as site specific exclusions. Furthermore, an ability to generate packets of electrons may eliminate the need for gates when such a device is in connection with an ion source for pulsed analytical stages, such as used in ion mobility spectrometers (IMS). According to an embodiment, the device 100 may include an electron emitter 120, high energy electron optics 130, and a thin membrane 140 disposed on an evacuated and sealed tube 110.

The electron emitter 120 may include a photocathode surface mounted on an optically transparent window that receives UV photons from an external source of UV photons according to an embodiment of the system described herein. For an example of an electron emitter that may be used in connection with the system described herein, reference is made to U.S. Pat. No. 7,576,320 to Bunker et al., entitled "Photoelectric Ion Source Photocathode Regeneration System," which is incorporated herein by reference. The transparent window, which may be made of sapphire and/or any other appropriate UV transparent material, may be mounted and sealed on the evacuated tube. In another embodiment, the transparent window may be part of a clear tube made out of sapphire or any appropriate UV transparent material on which a photocathode surface film may be deposited. Other embodiments using non-clear tubes having a transparent window mounted thereon may also be used. In various embodiments, the photocathode surface may be a solid, a mesh, a needle, or a wire made of electrically conducting material, such as a metal or a semiconductor, that emits electrons upon exposure to the UV photons.

Electrons emitted from the electron emitter 120 are then accelerated and/or focused within the evacuated tube 110 using the electron optics 130. In an embodiment, the electron optics 130 may include one or more electrodes, and may include successive electrodes biased at increasing voltages in order to achieve the final electron energy according to an embodiment of the system described herein. External or internal electron beam focusing such materials as magnetic thin films may be employed for electron confinement and directional control moving electrons toward the membrane 140.

The membrane 140 may be is made of a material transparent or semi-transparent to high energy (energetic) electrons. Upon impacting the membrane material, continuous or pulsed electron packets are partially transmitted through to a high pressure region such as atmospheric pressure. The range of electron energies emitted from the device 100 may be adjusted using the voltage of the electron optics 130, and properties of the membrane 140, such as thickness of the membrane material. The membrane may be a small thin film capable of withstanding the pressure difference between the inside and outside of the evacuated tube 110. In various embodiments, the membrane may be made of a non-metallic material, such as silicon nitride or other ceramics. The thickness of the membrane may be specified to permeate electrons with energies down to a certain cutoff value. For example, a membrane thickness of about 400 nm may be used to transmit electrons with energies of 10 keV and above.

Figure 2:
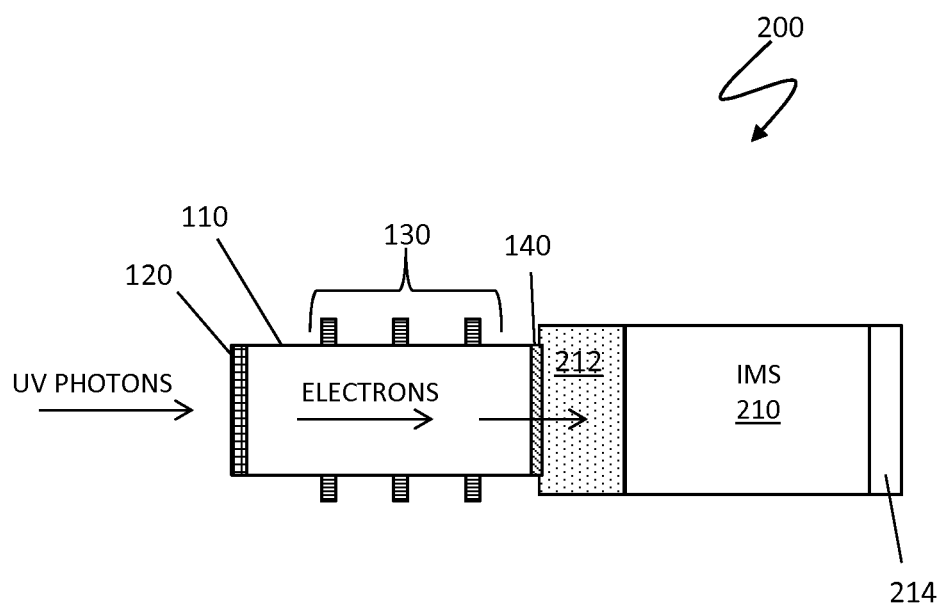
FIG. 2 is a schematic illustration showing a ion device using the high energy electron source device according to an embodiment of the system described herein.

FIG. 2 is a schematic illustration showing an ion device 200 using the high energy electron source device 100 according to an embodiment of the system described herein. The ion device 200 may include ion source and analytical components, such as used for chemical analysis in an ion mobility spectrometer (IMS) 210. Although the device 210 is principally identified herein as an IMS, it is noted that the system described herein may be used as an ion source in connection with any appropriate chemical detecting and analysis device that is based on ion mobilities, including, for example, differential mobility spectrometers (DMS) also called FAIMS devices. High energy electrons from the high energy electron source device 100 pass through the membrane 140 into an ionization zone 212. The high energy electrons ionize analyte molecules in the ionization zone 212 to yield reactant ions as an ion source.

Whereas the high energy electrons are accelerated in a vacuum using the electron optics 130 and transmitted through the membrane 140, the collisions of the high energy electrons with analyte molecules in the ionization zone 212, to yield the reactant ions, may be performed at atmospheric or near atmospheric pressure. The reactant ions may then be separated and used for chemical analysis of a sample with a detector/analyzer component 214 of the IMS 210. In various embodiments, the reactant ions may be subsequently used to transfer charge to sample ions of interest in a sample zone or the reactant ions, in some cases, may be the sample ions of interest to be analyzed with the IMS 210. By controlling use of high energy electron packets in connection with controlled collisions with analyte molecules, the use of gates for ion selection in an IMS may be reduced or eliminated. In various embodiments, the reactant ions from the ionization zone 212 may be separated using known techniques for IMS analysis that may include use of drift tubes and/or, in some cases, gating technologies, including the use of FAIMS devices that may be used in tandem with other IMS devices.

For specific descriptions of features and uses of IMS instruments, including use of one or more FAIMS devices that may be used in connection with ion detection and chemical analysis techniques, reference is made to U.S. Patent App. Pub. No. 2012/0273669 A1 to Ivashin et al., entitled "Chemical Analysis Using Hyphenated Low and High Field Ion Mobility" and U.S. Patent App. Pub. No. 2012/0326020 A1 to Ivashin et al., entitled "Ion Mobility Spectrometer Device with Embedded FAIMS," which are both incorporated herein by reference.

Figure 3:
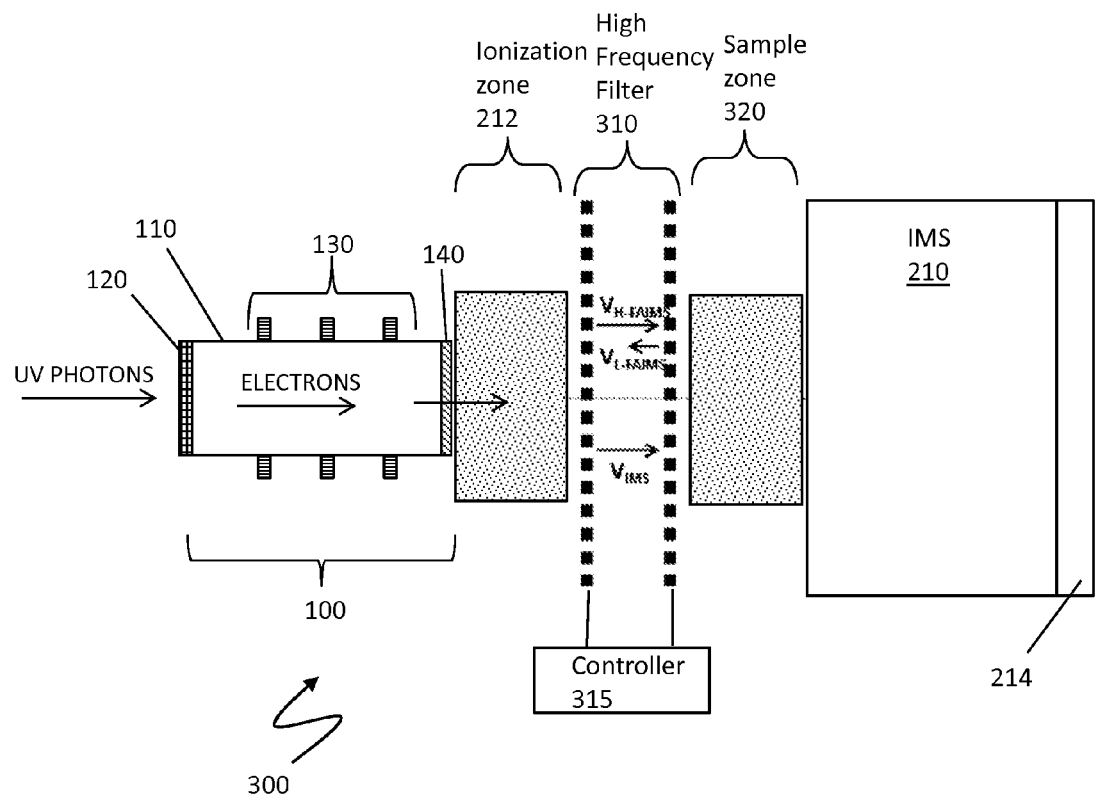
FIG. 3 is a schematic illustration showing an analysis device with an ion source provided according to the system described herein that provides ion analysis performed in connection with use of a FAIMS device.

FIG. 3 is a schematic illustration showing an analysis device 300 with an ion source provided according to the system described herein that provides ion analysis performed in connection with use of a FAIMS device. As discussed above, the system described herein may be used in with appropriate ion-mobility devices and techniques for ion separation and analysis, including the use of FAIMS devices. The device 300 may include the high energy electron source device 100 that supplies high energy electrons to the ionization zone 212 in which reactant ions are generated, as discussed elsewhere herein. In an embodiment, the reactant ions may be ionized components of air and/or other gas that is separate from a sample being analyzed. In the illustrated embodiment, a high frequency filter 310 may be positioned between the ionization zone 212 and a sample zone 320 that includes sample molecules of the sample being analyzed and where charge transfer occurs between the ions from the high frequency filter 310 and the sample molecules. From the sample zone 320, ions of interest may travel to the IMS device 210 having the detector/analyzer component 214 for analysis according to an embodiment of the system described herein. In various embodiments, it is further possible to perform ion separation in the IMS device 210, for example, with the use of a drift tube.

In various embodiments, the high frequency filter 310 may include a cell made of two parallel grids of various shapes, including cylindrical, spherical, and planar. In an embodiment, the filter may be a FAIMS cell. Within the cell, in the analytical gap between the grids, the combination of drift and high frequency asymmetric axial fields is applied. The grids are shown as planar grids, but, in other embodiments, the grids may be non-planar. The high frequency field alternates between high and low fields and subjecting ions to oscillations within the cell. Ions are either accelerated or decelerated depending on the nature of their high field mobility. Applying a small DC voltage can filter out specific ions on the basis of differences between their low and high field mobilities. In the illustrated embodiment, the high frequency filter 310 is shown situated between the ionization zone 212 where the reactant ions are formed using the high energy electrons, as discussed elsewhere herein, and the sample zone 320 where charge transfer occurs. By applying specific DC voltages, controlled by a controller 315, the high frequency filter may be used to control which reactant ions enter the sample zone 320 and which do not. Using such a filter, which can be adapted according to the properties of the sample molecules, one is able to control charge transfer yields in the sample zone. This method can be used to generate the ions of choice for subsequent analysis in such platforms as ion mobility and differential mobility spectrometers.

Ion velocities within the high frequency filter 310 are illustrated in the figure according to an embodiment of the system described herein. Ions are propelled from the ionization zone 212 to the FAIMS cell of the high frequency filter 310. Within the FAIMS cell, the ions are subject to electrostatic forces. $V_{ims}$ is the ion velocity due to the IMS field of the ionization zone that may propel the ions through the device 300. The controller 315 may control the field generated between the plates of the FAIMS cell according to the high field asymmetric waveform operation of the system described herein. $V_{FAIMS}$ is the net velocity of the ions due to the asymmetric waveform. $V_{FAIMS}$ may be calculated according to Equation 1:

$$V_{FAIMS} = V_{H\text{-}FAIMS} - V_{L\text{-}FAIMS} = K_H E_H - K_L E_L \quad \text{Eq. (1)}$$

where $V_{H\text{-}FAIMS}$ is the velocity and $K_H$ the mobility during the high field ($E_H$) and $V_{L\text{-}FAIMS}$ the velocity and $K_L$ the mobility during the low field ($E_L$).

The flight time through the FAIMS cell $T_{cell}$ is governed by the IMS field as well as the oscillations due to the FAIMS field. $T_{cell}$ can be derived from the following:

$$1/T_{cell} = 1/T_{IMS} + E_H T_H (K_H - K_L) / W \cdot (T_H + T_L) \quad \text{Eq. (2)}$$

$$T_{IMS} = W/K \cdot E_{IMS} \quad \text{Eq. (3)}$$

where W is the width of the cell, K is the IMS mobility, $T_H$ and $T_L$ are the duration of the high and low fields within the asymmetric waveform.

Figure 4:
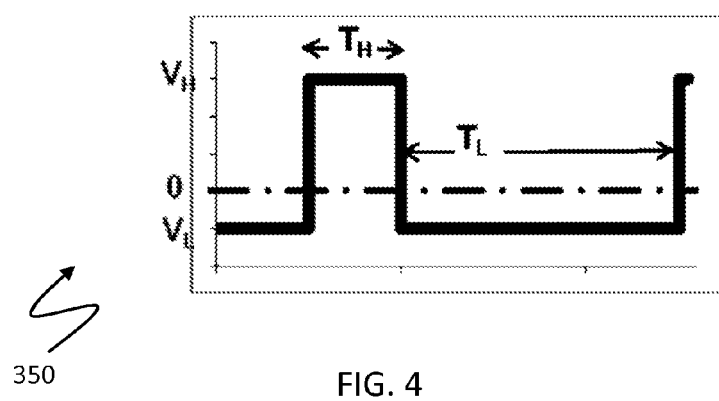
FIG. 4 is a plot showing parameters of an asymmetric waveform that may be used in connection with an embodiment of the system described herein.

FIG. 4 is a plot 350 showing parameters of an asymmetric waveform that may be used in connection with an embodiment of the system described herein. $T_H$ and $T_L$ show the duration of the high and low fields within the asymmetric waveform. Depending on the polarity of the waveform and the polarity of the difference between the high field and low field mobilities, $T_{cell}$ is either shorter or longer than $T_{IMS}$. Assuming the analysis of negative ions and assuming a positive waveform (the high field segment is positive while the low field segment is negative), type A ions (larger mobility at higher fields) move slower through the cell while type C (lower mobility at higher fields) ions move faster through the cell causing a few ms shifts in the IMS spectrum. Other FAIMS parameters that affect the transit time in the cell include the high field $E_H$ and the duty cycle of the asymmetric waveform $T_H/(T_H+T_L)$.

The shape of a drive waveform for a FAIMS cell of the high frequency filter is one of the features affecting FAIMS resolution, transmission, and separation. Due to practical circuitry advantages, FAIMS cells often employ a waveform formed by summing a sinusoidal wave and its first harmonic, at twice the frequency, resulting in first order Fourier approximation of an asymmetric square wave. It is noted that a rectangular drive waveform may be advantageous for FAIMS analyses. Analytical considerations show that rectangular waveforms may improve ion separation efficiency, resolution and/or sensitivity as compared to sinusoidal waveforms. Intuitively, use of an asymmetric square (and/or other rectangular) waveform for FAIMS would seem to maximize the differences during the high and low field portions of the electric field. These high to low periods of the waveform permit an ion to experience a maximum of unequal voltages maximizing the CV. However, in previous studies, there have been concerns that the time it takes an ion to respond to the idealized asymmetric square waveform and reach "steady state," or terminal, drift velocity might be sufficiently long to introduce error due to the transient electric field. It has been shown that, to the first order, this can be neglected if the time for reaching terminal velocity is small relative to the total drift time. Since the estimated time necessary to reach this velocity in a transient electric field is in the picosecond range and the drift time is in the millisecond range, this factor can therefore be ignored. In connection with generating waveforms for use with the system described herein, reference is made to, for example, E. V. Krylov, et al., "Selection and generation of waveforms for differential mobility spectrometry," Review of Scientific Instruments, 81, 024101 (2010), 11 pp., which is incorporated herein by reference.

The asymmetric waveform features a high voltage component causing the ion mobility to change with the field. As a consequence, a net change in the velocity of the ions, characteristic of the analyzed ions, results from the oscillations between high and low fields. Such a net change in the velocity may be either positive or negative for different ions. Depending on the nature of the mobility of the ions at high fields compared to that at low fields, the ions will either be accelerated or decelerated through the cell (and even including being stopped), thus causing the shift in their respective drift times that enables the desired ion separations for purposes of measurement. Accordingly, the high frequency filter 310, provided with a stream of ions obtained by operating an ionization source, may serve as a gate filtering ions or classes of ions depending on the value of a DC voltage (called compensation voltage) applied to either one of the FAIMS grids. Scanning such a DC voltage generates a spectrum.

Ion trajectories may be calculated using known techniques. For example, ion trajectories may be calculated using the Simion ray tracing package. A user program called Statistical Diffusion Simulation (SDS) is invoked by Simion to model the ion motion at atmospheric pressure. Reference is made to A. D. Appelhans and D. A. Dahl, "SIMION ion optics simulation at atmospheric pressure," Int. J. Mass. Spectrom, 244 (2005), pp. 1-14, which is incorporated herein by reference. The SDS code takes into account effects of high pressure collisions by modeling both diffusional and mobility terms of ions in a neutral gas. Ion dynamics are simulated by combined viscous ion mobility and random ion jumping (diffusion) approach. Space charge effects are not included in the SDS package and may be treated separately, for example, using the Coulomb Repulsion feature built into Simion.

Figure 5:
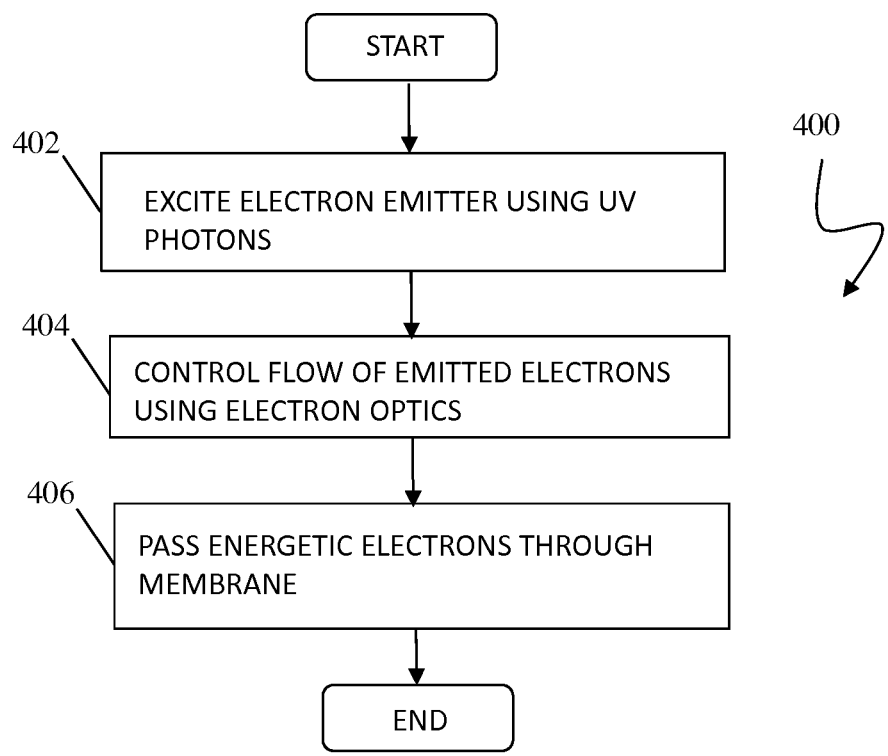
FIG. 5 is a flow diagram showing generation of high energy electrons in a high energy electron source that may be used in connection with an ion source, such as for an IMS device, according to an embodiment of the system described herein.

FIG. 5 is a flow diagram 400 showing generation of high energy electrons in a high energy electron source that may be used in connection with an ion source, such as for an IMS device, according to an embodiment of the system described herein. At a step 402, UV photons are used to excite a photocathode surface of an electron emitter. The photocathode surface may be mounted on a optically transparent portion of a sealed and evacuated tube. In various embodiments, the evacuated tube may be a transparent tube and/or may be a non-transparent tube having an optically transparent window disposed thereon. The photocathode surface may include a solid, a mesh, a needle, and/or a wire made of electrically conducting material, such as a metal or a semiconductor, that emits electrons upon exposure to the UV photons. After the step 402, in a step 404, emitted electrons from the electron emitted are accelerated through the evacuated tube using electron optics. The electron optics may include successive electrodes biased at increasing voltages that may be adjusted to control the final electron energies. After the step 404, in a step 406, high energy electrons pass through a membrane at the end of the evacuated tube. The high energy electrons that are emitted through the membrane may be controlled by properties of the membrane, including thickness of the membrane. After the step 406, processing of the high energy electron source for generating high energy electrons is complete. As further discussed, the high energy electrons may then be used in connection with an ion source for generating reactant ions used for sample analysis in an IMS device.

Figure 6:
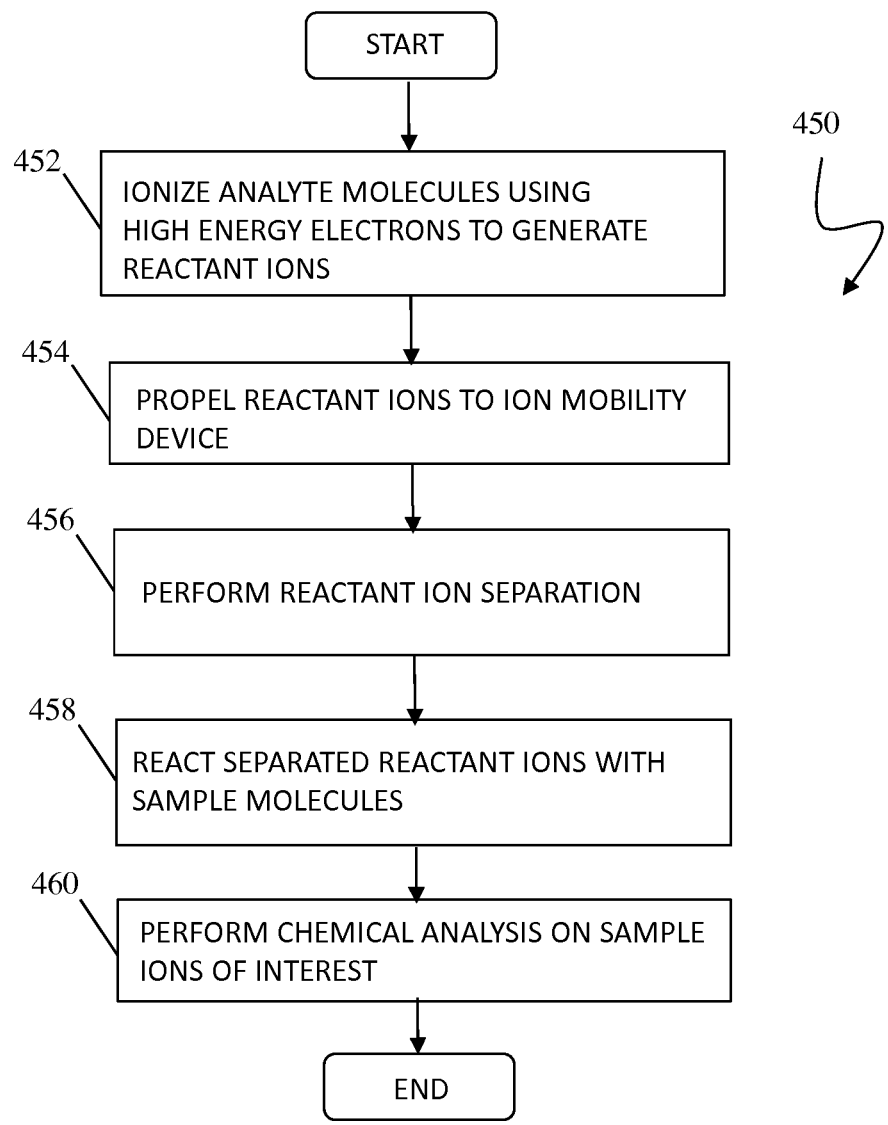
FIG. 6 is a flow diagram showing selective ionization processing steps using the high energy electrons produced from the flow diagram of FIG. 5 according to an embodiment of the system described herein.

FIG. 6 is a flow diagram 450 showing selective ionization processing steps using the high energy electrons produced from the flow diagram 400 according to an embodiment of the system described herein. In an embodiment, it is noted that the selective ionization may be performed in an ionization zone that is at atmospheric or near atmospheric pressure. At a step 452, components of an analyte gas (e.g., air and/or other appropriate gas) may be ionized by the high energy electrons emitted from the high energy electron source to generate reactant ions in the ionization zone. After the step 452, in a step 454, the reactant ions are propelled from the ionization zone to one or more ion-mobility components in connection with analysis of a sample material of interest. The ion-mobility components may include a drift tube for ion separation and/or a FAIMS (DMS) device.

After the step 454, in a step 456, ion separation is performed, such as using an IMS drift tube, and/or optional further filtering and/or gating of reactant ions may be performed. For example, in an embodiment, a high frequency filter (e.g., FAIMS filter) may be operated to separate at least some of the reactant ions in a process involving the use of oscillations of the ions, as further discussed elsewhere herein. After the step 456, in a step 458, selected reactant ions are reacted with sample molecules of a sample being analyzed in a charge transfer process in a reaction or sample zone. In various embodiments, the charge transfer process may include direct transfer of charge from the selected reactant ions to the sample molecules and/or may include attachment of the selected reactant ions to sample molecules to form molecular adducts or fragments via the attachment process and/or the dissociative attachment process. After the step 458, in a step 460, chemical analysis is performed on the generated sample ions of interest in an analytical component of an IMS device. After the step 460, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with other computers and/or with a user. Software implementations of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A high energy electron source device for ionization, comprising:
    an electron emitter disposed within an evacuated tube behind an optically transparent portion of the evacuated tube, wherein the electron emitter includes a photocathode element that emits electrons when excited by photons received at the photocathode element through the optically transparent portion of the evacuated tube;
    electron optics that control a flow of electrons along the evacuated tube, wherein the electron optics include a plurality of electrodes disposed along the evacuated tube, wherein the plurality of electrodes are biased to control a final electron energy of the electrons arriving at the membrane; and
    a membrane disposed at an end of the evacuated tube downstream from the flow of electrons caused by the electron optics, wherein the electrons arriving at the membrane from the electron optics pass through the membrane to yield high energy electrons, wherein the membrane has at least one property specified to permeate through the membrane the high energy electrons having energies down to a cutoff value such that a range of electron energies of the high energy electrons emitted from the membrane is adjustable using: (i) control of the voltages of the plurality of electrodes of the electron optics that determines an upper limit of the range of electron energies and (ii) the at least one property of the membrane that determines the lower limit of the range of electron energies according to the cutoff value.

2. The high energy electron source device according to claim 1, wherein the plurality of electrodes are biased at increasing voltages to control the final electron energy of the electrons arriving at the membrane.

3. The high energy electron source device according to claim 1, wherein the photocathode element is a photocathode surface film deposited on the optically transparent portion of the evacuated tube.

4. The high energy electron source device according to claim 1, wherein the photocathode element is at least one of: a solid, a mesh, a needle, or a wire made of electrically conducting material.

5. The high energy electron source device according to claim 1, wherein the evacuated tube is a transparent tube made of a UV transparent material.

6. The high energy electron source device according to claim 1, wherein the evacuated tube is a non-transparent tube having a transparent window as the optically transparent portion.

7. The high energy electron source device according to claim 1, wherein the membrane is a non-metallic thin film.

8. A method for producing high energy electrons for ionization, comprising:

exciting an electron emitter disposed within an evacuated tube behind an optically transparent portion of the evacuated tube, wherein the electron emitter includes a photocathode element that emits electrons when excited by photons received at the photocathode element through the optically transparent portion of the evacuated tube;

controlling a flow of the electrons along the evacuated tube using electron optics, wherein the electron optics include a plurality of electrodes disposed along the evacuated tube, wherein the plurality of electrodes are biased to control a final electron energy of the electrons arriving at the membrane; and passing the electrons through a membrane disposed at an end of the evacuated tube downstream from the flow of electrons caused by the electron optics, wherein the electrons that pass through the membrane are high energy electrons, wherein the membrane has at least one property specified permeate through the membrane the high energy electrons having energies down to a cutoff value such that a range of electron energies of the high energy electrons emitted from the membrane is adjustable using: (i) control of the voltages of the plurality of electrodes of the electron optics that determines an upper limit of the range of electron energies and (ii) the at least one property of the membrane that determines the lower limit of the range of electron energies according to the cutoff value.

9. The method according to claim 8, wherein the plurality of electrodes are biased at increasing voltages to control the final electron energy of the electrons arriving at the membrane.

10. The method according to claim 8, wherein the photocathode element is a photocathode surface film deposited on the optically transparent portion of the evacuated tube.

11. The method according to claim 8, wherein the photocathode element is at least one of: a solid, a mesh, a needle, or a wire made of electrically conducting material.

12. The method according to claim 8, wherein the evacuated tube is a transparent tube made of a UV transparent material.

13. The method according to claim 8, wherein the evacuated tube is a non-transparent tube having a transparent window as the optically transparent portion.

14. The method according to claim 8, wherein the membrane is a non-metallic thin film.

15. The high energy electron source device according to claim 1, wherein the high energy electrons passing through the membrane are controllably provided as continuous or pulsed electron packets according to exposure of the photocathode element to the photons.

16. The high energy electron source device according to claim 1, wherein the high energy electrons passing through the membrane enable ionization, using the high energy electron source device as a non-radioactive electron source, of atomic or molecular species at atmospheric or near atmospheric pressure for subsequent ion analysis.

17. The high energy electron source device according to claim 1, further comprising:
a UV photon source that generates the photons received at the photocathode element through the optically transparent portion of the evacuated tube.

18. The method according to claim 8, wherein the high energy electrons passing through the membrane are controllably provided as continuous or pulsed electron packets according to exposure of the photocathode element to the photons.

19. The method according to claim 8, wherein the high energy electrons passing through the membrane enable ionization, using a non-radioactive electron source, of atomic or molecular species at atmospheric or near atmospheric pressure for subsequent ion analysis.

20. The method according to claim 8, further comprising:
a UV photon source that generates the photons received at the photocathode element through the optically transparent portion of the evacuated tube.

21. The high energy electron source device according to claim 1, wherein the at least one property of the membrane includes a thickness of the membrane.

22. The high energy electron source device according to claim 1, wherein the membrane is made of silicon nitride.

23. The method according to claim 8, wherein the at least one property of the membrane includes a thickness of the membrane.

24. The method according to claim 8, wherein the membrane is made of silicon nitride.

* * * * *